United States Patent [19]

Hebborn

[11] Patent Number: 5,480,399
[45] Date of Patent: Jan. 2, 1996

[54] ELECTROSURGERY MONITOR AND APPARATUS

[75] Inventor: Kevin A. Hebborn, Hove, England

[73] Assignee: Smiths Industries Public Limited Company, London, United Kingdom

[21] Appl. No.: 212,739

[22] Filed: Mar. 14, 1994

[30] Foreign Application Priority Data

Mar. 30, 1993 [GB] United Kingdom ............... 9306637

[51] Int. Cl.⁶ .................................................. A61B 17/39
[52] U.S. Cl. ........................................... 606/35; 128/908
[58] Field of Search .................... 606/35, 32; 128/908

[56] References Cited

U.S. PATENT DOCUMENTS

| | | | |
|---|---|---|---|
| 4,171,700 | 10/1979 | Farin | 128/303.14 |
| 4,200,104 | 4/1980 | Harris | 606/35 |
| 4,244,371 | 1/1981 | Farin | 128/303.14 |
| 4,416,277 | 11/1983 | Newton et al. | 128/303.13 |
| 4,494,541 | 1/1985 | Archibald | 606/35 |
| 4,848,335 | 7/1989 | Manes | 606/35 |

FOREIGN PATENT DOCUMENTS

| | | |
|---|---|---|
| 0336742 | 10/1989 | European Pat. Off. . |
| 2646229 | 4/1878 | Germany . |
| 3239640 | 5/1983 | Germany . |
| 1333573 | 10/1973 | United Kingdom . |
| 2266817 | 11/1993 | United Kingdom . |

Primary Examiner—Lee S. Cohen
Attorney, Agent, or Firm—Pollock, Vande Sande and Priddy

[57] ABSTRACT

A monitor for the return electrode of electrosurgery apparatus has three contacts in a socket that connect with two or three contacts on a plug connected to the return electrode. One pair of contacts in the socket is connected across an oscillator that provides an output to a first primary winding of the transformer when there is a low impedance between the contacts. Another pair of contacts is connected across a second primary, winding and produces a loading on the transformer when short circuited by the return electrode, A detector is connected to the secondary winding of the transformer and produces an alarm and disable signal if the signal on the secondary winding falls below a lower limit or exceeds an upper limit, 10 Claims, 3 Drawing Sheets

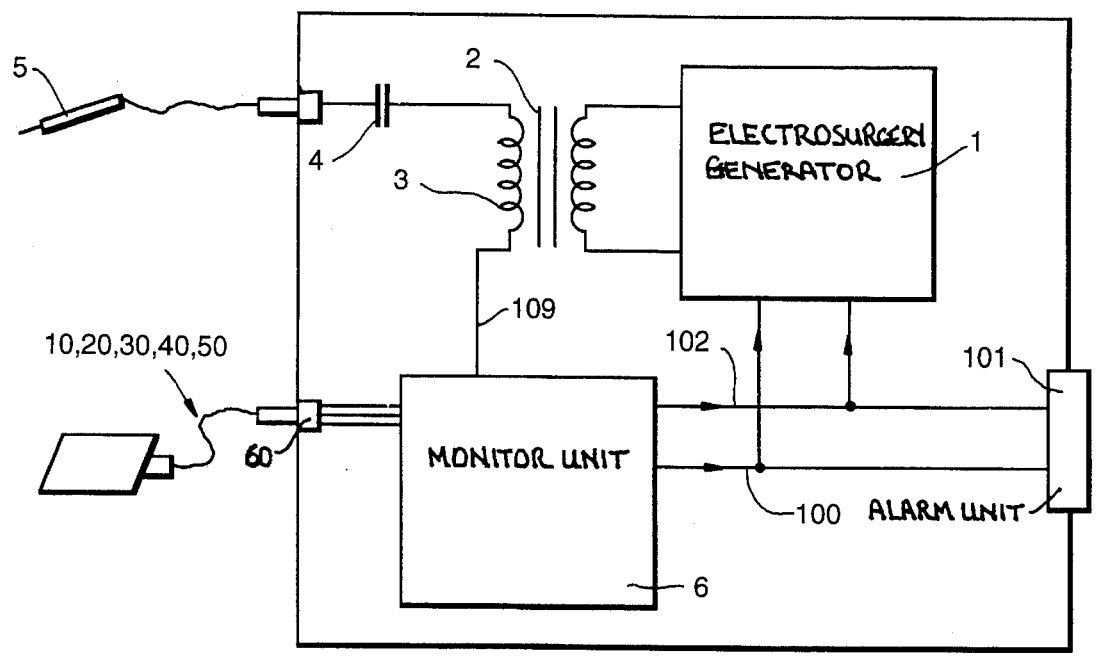
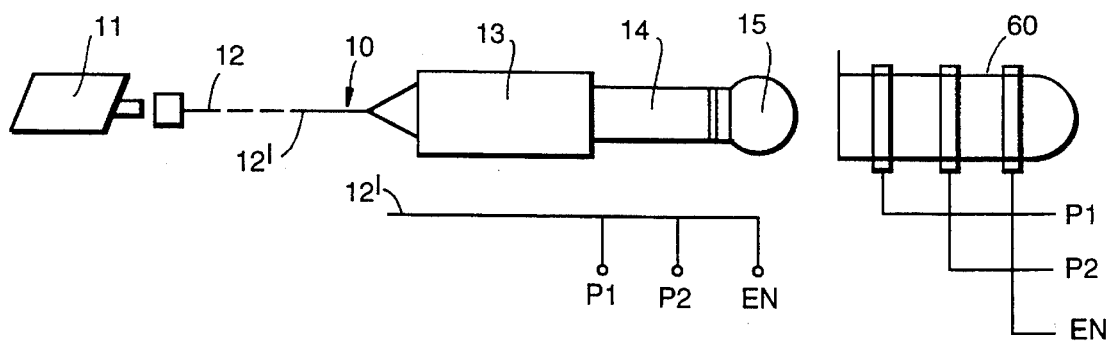
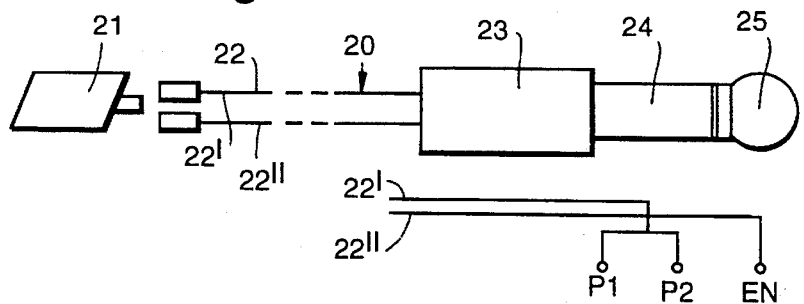

5,480,399

ELECTROSURGERY MONITOR AND APPARATUS

BACKGROUND OF THE INVENTION

This invention relates to electrosurgery monitors and apparatus.

Electrosurgery apparatus, such as diathermy apparatus, employs high frequency RF energy to produce a surgical cutting or coagulation effect, or a combination of these effects. The energy is applied to the patient via a hand-held, patient electrode, which concentrates the energy in a small region so that the current density in that region is sufficiently high to produce the desired effect. Energy is returned to the electrosurgery unit via a large area, return electrode in the form of a flexible plate attached to the body. The large area of contact of the return electrode with the patient's skin ensures that the electrosurgery energy at the underlying skin surface has a much lower current density; in this way, no electrosurgery effect is produced at the return electrode.

A problem occurs with electrosurgery apparatus if the return electrode is not connected to the apparatus, since there will be no return path via the apparatus; this can lead to RF energy returning to ground via an alternative route. There is also a problem if the return electrode becomes loose, or if contact with the skin is reduced for some other reason, such as drying of the conductive gel used between the electrode and the skin; this can result in a more localized contact of the return plate with the skin. In both cases, a higher return current density may result, which in turn can produce burning of the skin.

In order to reduce the risk of burn injury to the patient, it is common practice for the electrosurgery apparatus to include some form of monitor to detect incorrect connection of the return electrode to the apparatus and separation of the return electrode from the skin. Because of the different forms that return electrodes can take, it can be difficult to provide a monitor that can be used safely with different return electrodes.

BRIEF SUMMARY OF THE INVENTION

It is an object of the present invention to provide an improved electrosurgery monitor and apparatus.

According to one aspect of the present invention there is provided an electrosurgery monitor assembly including a monitor unit, a large area return electrode, and a cable connected at one end to the electrode and at its other end to a connector, the monitor unit including at least a first and second input connection adapted to make electrical connection with the connector, an oscillator having an input coupled with the two input connections such that the output of the oscillator is dependent on a connection being established between the two input connections, and detector means responsive to the output of the oscillator to provide an alarm signal in the event of the absence of a correct connection at the input connections.

The monitor unit preferably includes a transformer, the oscillator being connected to provide an alternating input to a primary winding of the transformer when there is a low impedance between the two input connections, and the detector means being connected to a secondary winding of the transformer and providing the alarm signal when the signal in the secondary winding falls below a predetermined value. The monitor unit preferably includes a third input connection, the second and third connections being connected to a second primary winding of the transformer, the detector means being arranged also to produce an alarm signal in the event of an output of oscillator being above an upper threshold value, and the connector being arranged to produce a low impedance across the second and third connections so that the second primary winding produces a loading on the transformer that reduces the output on the secondary winding below the upper threshold value. The assembly may include a further oscillator and a further transformer, the first oscillator being powered by the further oscillator via the transformer. The alarm signal may be arranged to interrupt supply of electrosurgery power to the patient. The input connections may be spaced along the length of a socket, the connector being a plug and the connector having contacts spaced along the length of the plug.

The return electrode may be a single-plate electrode, the cable being a single-lead cable, and the connector having two contacts connected to the single lead. Alternatively, the return electrode may be a single-plate electrode, the cable being a double-lead cable and the connector having two contacts connected to respective ones of the leads in the cable connected together at the electrode. Alternatively, the return electrode may be a single-plate electrode, the cable being a triple-lead cable, and the connector having three contacts connected to respective ones of the leads in the cable and connected together at the electrode. Alternatively, the return electrode may be a split-plate electrode, the cable being a double-lead cable, the two leads in the cable being connected to respective parts of the split-plate electrode and the connector having a first contact connected to one lead and a second contact connected to the other lead.

According to another aspect of the invention there is provided electrosurgery apparatus including an electrosurgery generator, an active electrode and a monitor assembly according to the above one aspect of the invention.

Electrosurgery apparatus including a monitor according to the present invention, will now be described, by way of example, with reference to the accompanying drawings.

BRIEF DESCRIPTION OF THE DRAWINGS

FIG. 1 is a schematic diagram of the electrosurgery apparatus;

FIGS. 3A to 3E show different forms of return electrode assembly.

DETAILED DESCRIPTION OF THE PREFERRED EMBODIMENTS

Figure 2:
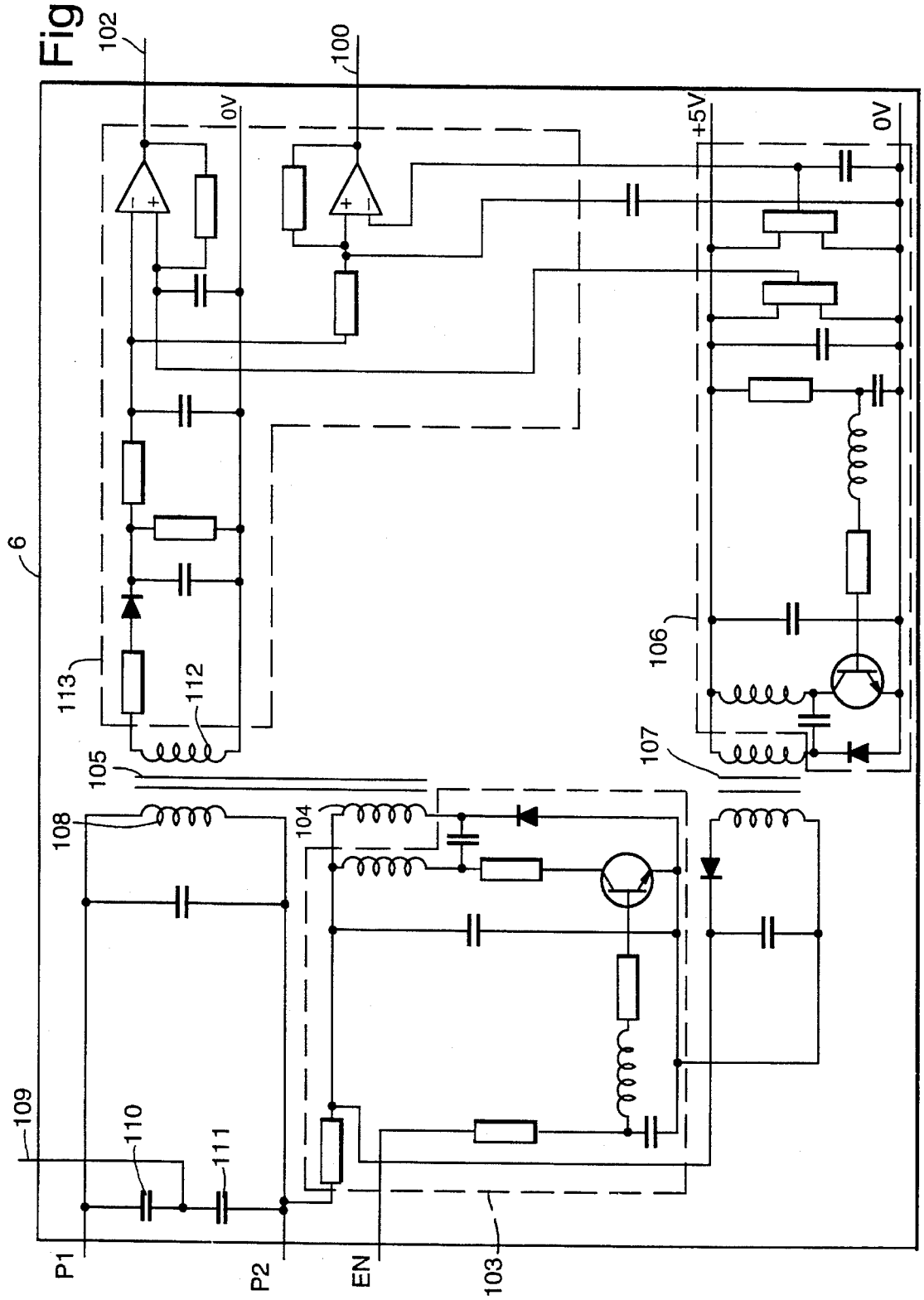
FIG. 2 shows the monitor unit of the apparatus in greater detail.

With reference first to FIG. 1, the apparatus includes an electrosurgery generator 1 of conventional construction supplying high frequency RF electrosurgery energy to a transformer 2. One end of the secondary winding 3 of the transformer is connected via a capacitor 4 to an active hand-held electrode 5. The other end of the secondary winding 3 is connected via a monitor unit 6 to a return electrode assembly 10, 20, 30, 40 or 50.

With reference now also to FIGS. 2 and 3, the monitor unit 6 is connected to three contacts $P_1$, $P_2$ and EN (enable) in a socket 60 on the casing of the apparatus. The contacts are spaced apart from one another along the length of the socket in the manner shown in FIG. 3A. The monitor unit 6 provides an alarm signal on line 100 to an alarm unit 101 when the monitor unit detects that the return electrode is not connected. A second alarm signal is given on line 102 to the alarm unit 101 when the monitor 6 detects that the return electrode is not correctly attached to the patient.

The monitor unit 6 includes a first oscillator 103, which normally provides an alternating output to a primary winding 104 of a transformer 105. The first oscillator 103 derives its operating power from a second oscillator 106 via an isolating transformer 107. This arrangement ensures isolation of the patient from mains power. The first oscillator 103 has a control input connected across the contacts $P_2$ and EN of the socket 60 and only provides an output when $P_2$ and EN are connected together by a low impedance.

The contacts $P_1$ and $P_2$ in the socket 60 are connected to opposite ends of a second primary winding 108 of the transformer 105. The electrosurgery return current is taken on line 109, which is connected to the junction of a series connection of two capacitors 110 and 111 between the two contacts $P_1$ and $P_2$. Line 109 is connected to the secondary winding 3 of the transformer 2.

The transformer 105 has a secondary winding 112 connected to a detector unit 113. The detector unit 113 responds to a signal in the secondary winding 112 below a first threshold $V_L$ by producing an alarm signal on line 100 to indicate that the return electrode assembly has not been connected. If the signal in the secondary winding 112 rises above a second, high-level threshold $V_u$, the detector 113 produces an alarm signal on line 102 to indicate that the return electrode is not correctly attached to the patient.

If either the first oscillator 103 or the second oscillator 106 should fail, this would result in the absence of a signal on the primary winding 104 and hence cause the detector unit 113 to produce an alarm output on line 100.

The return electrode assembly 10, 20, 30, 40 or 50 may take any one of the five different forms illustrated in FIGS. 3A to 3E.

FIG. 3A shows an assembly 10 with a single plate electrode 11 connected by a connector to one end of a single-lead cable 12. The other end of the cable is connected to a male coupling or plug 13 having two contacts 14 and 15, both of which are connected to the same lead 12' in the cable. The plug 13 makes connection with the socket 60, the spacing of the contacts being such that contacts $P_1$ and $P_2$ both make connection to the same contact 14 on the plug. The other contact EN makes connection with a second contact 15 at the tip of the plug.

In operation, it can be seen that contacts $P_2$ and EN will be shorted at the plug 13 when this is inserted correctly in the socket 60, so that the oscillator 103 will operate and provide an output to the primary winding 104, which in turn produces an output on the secondary winding 112. The other primary winding 108 is effectively short circuited by the contact 14, which bridges the contacts $P_1$ and $P_2$ in the socket 60. The winding 108 thereby provides a loading on the transformer 105 reducing the output at the secondary winding 112 to a level below the upper threshold $V_u$ but above the lower threshold $V_L$. In this state, no alarm output is produced. If, however, the plug 13 were inadvertently pulled out of the socket 60, this would cause a high impedance across the contacts $P_2$ and EN and cause the oscillator 103 to stop functioning. The output of the secondary winding 112 would then drop below the lower threshold $V_L$ and cause the detector 113 to produce an alarm on line 100. This in turn would cause the alarm unit 101 to provide a warning signal indicative of disconnection, which causes a buzzer and/or lamp in the unit to be energized. The signal on line 100 is also supplied to the generator 1 to interrupt supply of power to the hand-held electrode 5.

In this arrangement, the monitor unit 6 would not be able to detect if the return electrode 11 became detached from the patient or if the cable 12 became detached from the electrode.

FIG. 3B shows a return electrode assembly 20 with a single plate electrode 21 connected by a double-lead cable assembly 22 to a two-contact plug 23 of the same kind as that shown in FIG. 3A. One of the leads 22' of the cable is connected to the contact 24, which makes connection with the contacts $P_1$ and $P_2$ in the socket 60. The other lead 22" is connected to the tip contact 25, which makes connection with the contact EN in the socket 60. At the other end of the cable assembly 22, because the two leads 22' and 22" are connected to the same plate electrode 21, they are effectively short circuited.

In this arrangement, the contacts $P_2$ and EN will be bridged by the circuit between the two leads 22' and 22" and the short-circuiting of the two leads at their connection to the electrode 21. The monitor unit 6 responds in a similar way to the assembly 10 but it will also be able to detect disconnection of the electrode 21 from the cable 22 because this will break the circuit between the two leads and hence between the contacts. This will cause a disconnection alarm to be produced on line 100.

Figure 3C:
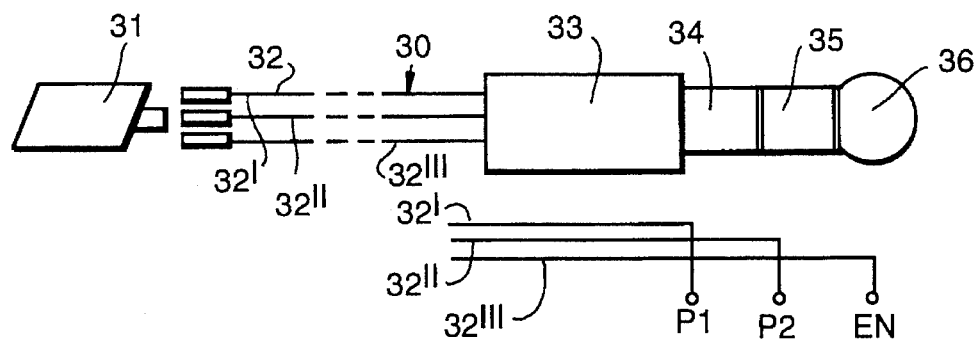

FIG. 3C shows an assembly 30 with a single plate return electrode 31 connected by a triple-lead cable assembly 32 to a three-contact plug 33. The three contacts 34, 35 and 36 of the plug 33 make connection with respective ones of the three leads 32', 32" and 32''' in the cable 32. The contacts 34, 35 and 36 make connection with respective ones of the contacts $P_1$, $P_2$ and EN in the socket 60 when the plug 33 is inserted. At the opposite end of the cable assembly 32 each of the three leads is connected to the same plate, thereby effectively short-circuiting the leads at the patient end.

The monitor unit 6 will be able to respond to disconnection of the assembly 30 either at the apparatus or at the return plate electrode 31, in the same way as with the electrode assembly 20 shown in FIG. 3B.

Figure 3D:
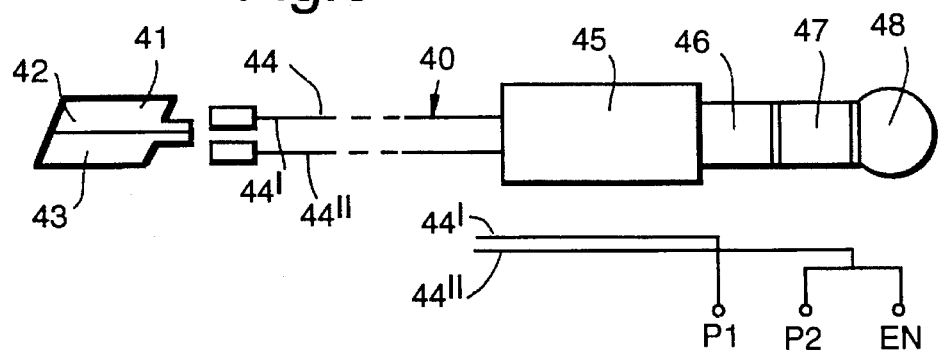

FIG. 3D shows an assembly 40 with a split-plate electrode 41 having two electrode regions 42 and 43 electrically isolated from one another. The electrode 41 is connected by a double-lead cable assembly 44 to a three-contact plug 45. One of the leads 44' of the cable is connected at one end to the contact 46, which makes connection with contact $P_1$ in the socket, and at the other end to one of the electrode regions 42. The other of the leads 44" is connected at one end to both contacts 47 and 48, which make connection with the contacts $P_2$ and EN in the socket 60. At its other end, the lead 44" is connected to the other of the electrode regions 43.

With this cable assembly 40, the contacts $P_2$ and EN are bridged at the plug 45 so that no disconnect alarm will be produced as long as the plug remains inserted in the socket 60. While the electrode 41 remains in good electrical contact with the skin of the patient there is a relatively low impedance between the two regions 42 and 43. This ensures that the primary winding 108 of the transformer 105 gives an appreciable loading to the transformer so that the output of the secondary winding 112 is maintained below the upper threshold value $V_u$. If, however, the electrode 41 should become detached from the skin this would increase the impedance between the two electrode regions 42 and 43 and hence increase the impedance between the contacts $P_1$ and $P_2$. Consequently, the loading of the transformer 105 would be reduced and the output on the secondary winding 112 would increase above the upper threshold $V_u$. This would cause the detector unit 113 to produce a signal on line 102 to indicate that the return electrode plate is not attached to the patient. It will be appreciated that, if the electrode 41 should become disconnected from the patient end of the cable 44, this would also lead to an increase in the impedance across the contacts $P_1$ and $P_2$ and hence give an alarm indicative of detachment of the plate from the skin.

Figure 3E:
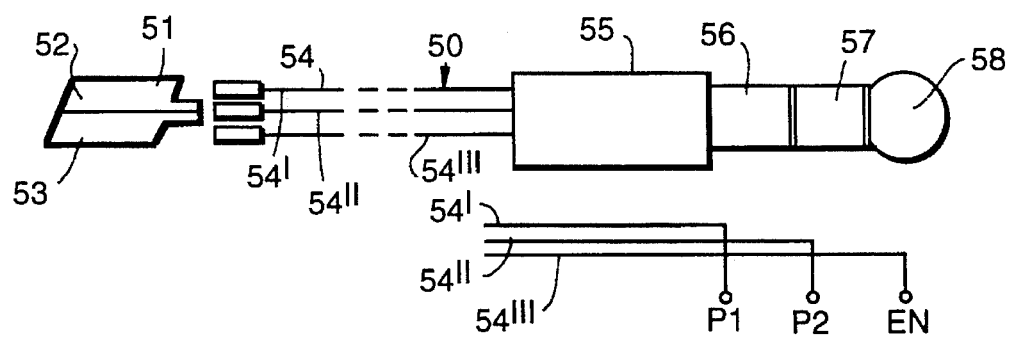

FIG. 3E shows an assembly 50 with a split-plate electrode 51, of the same kind as shown in FIG. 3D, having two electrode regions 52 and 53 electrically isolated from one another. The electrode 51 is connected by a triple-lead cable assembly 54 to a three-contact plug 55. One of the leads 54' of the cable 54 is connected, at one end, to a contact 56 in the plug 55, which makes connection with contact $P_1$ in the socket 60. At its other end, the lead 54' makes connection to one of the electrode regions 52. A second lead 54" in the cable is connected, at one end, to a contact 57 in the plug, which makes connection with contact $P_2$ in the socket 60. At its other end, the second lead 54" is connected to the other electrode region 53. The third lead 54''' is connected, at one end, to a contact 58 in the plug 55, which makes connection with the contact EN in the socket 60. At its other end, the third lead 54''' is connected to the same electrode region 53 as the second lead 54".

With this return electrode assembly 50, the monitor unit 6 will operate in a similar way to that when used with the assembly 40. However, with the assembly 50, there is a difference in that, if the plate 51 should become disconnected from the cable 54 at the patient end connector, this would break the circuit between the contacts $P_2$ and EN and thereby prevent operation of the oscillator 103. This would cause the output of the secondary winding 112 to drop below $V_L$ and hence cause the detector unit 113 to produce an alarm signal on line 100 indicative of the absence of a connection.

It can be seen, therefore, that the electrosurgery apparatus can be used safely with all five different forms of return electrode assembly.

What I claim is:

1. An electrosurgery monitor assembly comprising: a monitor unit; a large area return electrode; a cable; and a connector, the cable being connected at one end to the electrode and at its other end to the connector, wherein the monitor unit includes first, second and third input connections making electrical connection with the connector, a first oscillator, said oscillator having an input coupled with said first and second input connections such that an output of said oscillator is dependent on a connection being established between said first and second input connections, and detector means responsive to the output of said oscillator to provide an alarm signal in the event of the absence of a correct connection at said first and second input connections; said monitor unit including a first transformer, means connecting the output of said oscillator to a primary winding of said first transformer so as to provide an alternating input to said primary winding when there is a low impedance between said first and second input connections, said detector means being connected to a secondary winding of the first transformer and providing said alarm signal when the signal in the secondary winding falls below a predetermined value, and means connecting said second and third connections to a second primary winding of the first transformer, said detector means also producing an alarm signal if the output of said oscillator is above an upper threshold value, said connector providing a low impedance across said second and third connections so that the second primary winding produces a loading on the first transformer that reduces the output on said secondary winding below the upper threshold value.

2. An electrosurgery monitor assembly comprising: a monitor unit; a large area return electrode; a cable; and a connector, the cable being connected at one end to the return electrode and at its other end to the connector, the monitor unit including at least two input connections making electrical connection with the connector, a first oscillator having an input and an output, said first oscillator input being coupled with said two input connections such that the output of said first oscillator is dependent on a connection being established between said two input connections, a second oscillator and a transformer, said first oscillator being powered by said second oscillator via said transformer, and detector means responsive to the output of said first oscillator to provide an alarm signal in the event of the absence of a correct connection at said two input connections.

3. An electrosurgery monitor assembly comprising: a monitor unit; a large area return electrode; a cable; and a connector, the cable being connected at one end to the return electrode and at its other end to the connector, the monitor unit including at least two input connections making electrical connection with the connector, the input connections being spaced along the length of a socket, the connector being a plug having contacts spaced along the length of the plug, an oscillator having an input and an output, said oscillator output being coupled with said two input connections such that the output of said oscillator is dependent on a connection being established between said two input connections, and detector means responsive to the output of said oscillator to provide an alarm signal in the event of the absence of a correct connection at said two input connections.

4. An electrosurgery monitor assembly comprising: a monitor unit; a large area split-plate return electrode; a triple-lead cable; and a connector, first ends of two leads of said cable being connected to respective parts of said split-plate electrode and a first end of a third lead being connected to the same part of the electrode as one of the other leads, said connector having a first contact connected to a second end of one lead, a second contact connected to a second end of another lead and a third contact connected to a second end of the third lead, the monitor unit including at least two input connections making electrical connection with the connector, an oscillator having an input and an output, said oscillator input being coupled with said two input connections such that the output of said oscillator is dependent on a connection being established between said two input connections, and detector means responsive to the output of said oscillator to provide an alarm signal in the event of the absence of a correct connection at said two input connections.

5. An assembly according to one of claims 1, 2, 3 or 4 including means for interrupting supply of electrosurgery power to a patient in response to said alarm signal.

6. An assembly according to claim 2 or 3, wherein said return electrode is a single plate electrode, wherein said cable is a double-lead cable, and wherein said connector has two contacts connected to respective ones of leads in the cable and connected together at said electrode.

7. An assembly according to claim 2 or 3, wherein said return electrode is a single plate electrode, wherein said cable is a triple-lead cable, and wherein said connector has three contacts connected to respective ones of leads in the cable and connected together at said electrode.

8. An assembly according to claim 2 or 3, wherein said return electrode is a split-plate electrode, wherein said cable is a double-lead cable, wherein two leads in the cable are connected to respective pans of said split-plate electrode, and wherein said connector has a first contact connected to one lead and a second contact connected to the other lead.

9. (Amended) An electrosurgery monitor assembly comprising:

a monitor unit;

a large area return electrode;

a cable; and a connector, said cable being connected at one end to the electrode and at its other end to the connector, wherein the monitor unit includes three input connections making electrical connection with the connector;

a transformer having first and second primary windings and a secondary winding;

an oscillator having two inputs coupled respectively with a first and second of said input connections, said oscillator having an output connected to the first primary winding, the oscillator producing an output signal to the first primary winding only when there is a low impedance across the first and second input connections;

means connecting the second and third input connections across the second primary winding so that the second primary winding produces a loading on the transformer when the connector produces a low impedance across the second and third input connections;

a detector; and means connecting said detector across said secondary winding of the transformer, said detector producing an alarm signal if the signal on said secondary winding is below a lower limit or above an upper limit.

10. Electrosurgery apparatus comprising:

an electrosurgery generator;

an active electrode;

means connecting said active electrode to said generator; and a monitor assembly comprising;

a monitor unit;

a large area return electrode;

a cable; and a connector, said cable being connected at one end to the electrode and at its other end to the connector, wherein the monitor unit includes three input connections making electrical connection with the connector;

a transformer having first and second primary windings and a secondary winding;

an oscillator having two inputs coupled respectively with a first and second of said input connections, said oscillator having an output connected to the first primary winding, the oscillator producing an output signal to the first primary winding only when there is a low impedance across the first and second input connections;

means connecting the second and third input connections across the second primary winding so that the second primary winding produces a loading on the transformer when the connector produces a low impedance across the second and third input connections;

a detector; and means connecting said detector across said secondary winding of the transformer, said detector producing an alarm signal to said generator if the signal on said secondary winding is below a lower limit or above an upper limit.

* * * * *